(12) United States Patent
James

(10) Patent No.: US 12,702,611 B2
(45) Date of Patent: Aug. 11, 2026

(54) RADIOLUCENT SENSOR EMI SHIELDING

(71) Applicant: MIZUHO ORTHOPEDIC SYSTEMS, INC., Union City, CA (US)

(72) Inventor: Paul James, Santa Clara, CA (US)

(73) Assignee: Mizuho Orthopedic Systems, Inc., Union City, CA (US)

( * ) Notice: Subject to any disclaimer, the term of this patent is extended or adjusted under 35 U.S.C. 154(b) by 855 days.

(21) Appl. No.: 18/073,154

(22) Filed: Dec. 1, 2022

(65) Prior Publication Data

US 2024/0180766 A1 Jun. 6, 2024

(51) Int. Cl.
*A61G 13/12* (2006.01)
*A61B 18/16* (2006.01)
*A61B 18/00* (2006.01)

(52) U.S. Cl.
CPC ............ *A61G 13/126* (2013.01); *A61B 18/16* (2013.01); *A61B 2018/00595* (2013.01); *A61G 2203/34* (2013.01); *A61G 2203/70* (2013.01)

(58) Field of Classification Search
CPC .......... A61B 18/16; A61B 2018/00595; A61G 13/10; A61G 13/126; A61G 13/1285; A61G 2203/34; A61G 2203/70
See application file for complete search history.

(56) References Cited

U.S. PATENT DOCUMENTS 5,815,864 A * 10/1998 Sloop ................ A61G 7/05769 5/713
6,653,607 B2 11/2003 Ellis et al.
6,924,467 B2 8/2005 Ellis et al.
7,752,926 B2 7/2010 Caminade et al.
7,822,462 B2 10/2010 Elias
8,264,342 B2 9/2012 Blair et al.
8,633,827 B2 1/2014 Lakshminarayanan
8,782,832 B2 7/2014 Blyakher et al.
8,878,668 B2 11/2014 Blair et al.
(Continued)

FOREIGN PATENT DOCUMENTS

CN 105726056 B 12/2019
CN 111372547 A 7/2020
(Continued)

OTHER PUBLICATIONS

International Search Report and Written Opinion dated Feb. 7, 2024 for PCT/US23/34929.
(Continued)

*Primary Examiner* — Khadijeh A Vahdat
(74) *Attorney, Agent, or Firm* — Reed Smith LLP; Matthew P. Frederick; Jennifer C. Black

(57) ABSTRACT

A radiolucent pressure-sensing mattress for a surgical table includes radiolucent pressure sensors, and a radiolucent electromagnetic interference shielding layer. The radiolucent pressure sensors measure the amount of force exerted
(Continued)

by a patient's body at certain locations of the radiolucent pressure-sensing mattress. The radiolucent electromagnetic interference shielding layer envelopes the radiolucent pressure sensors. The shielding layer shields the sensors from electromagnetic interference from other sources in an operating room. In certain embodiments, the shielding layer is made from woven carbon fiber.

20 Claims, 4 Drawing Sheets

(56) References Cited

U.S. PATENT DOCUMENTS

| | | | | |
|---|---|---|---|---|
| 8,904,876 | B2 | 12/2014 | Taylor et al. | |
| 9,050,235 | B2 | 6/2015 | Blair et al. | |
| 9,730,850 | B2 | 8/2017 | Blair et al. | |
| 9,962,122 | B2 | 5/2018 | Augustine et al. | |
| 10,206,248 | B2 | 2/2019 | Augustine et al. | |
| 10,369,067 | B2 | 8/2019 | Blair et al. | |
| 10,416,031 | B2 | 9/2019 | Hsu et al. | |
| 2001/0032362 | A1* | 10/2001 | Welling | A61G 7/052 5/600 |
| 2001/0040496 | A1 | 11/2001 | Wang et al. | |
| 2003/0061661 | A1 | 4/2003 | Borders et al. | |
| 2003/0153805 | A1 | 8/2003 | Gryn et al. | |
| 2004/0199072 | A1* | 10/2004 | Sprouse | A61B 5/062 5/601 |
| 2006/0191886 | A1 | 8/2006 | Pak | |
| 2012/0017376 | A1 | 1/2012 | Mikkelsen et al. | |
| 2015/0290065 | A1* | 10/2015 | Augustine | A61G 7/05 5/655.3 |
| 2016/0143091 | A1* | 5/2016 | Augustine | A61B 18/16 219/528 |
| 2017/0135855 | A1 | 5/2017 | Stefan et al. | |
| 2017/0325683 | A1* | 11/2017 | Larson | A61B 5/1113 |
| 2020/0360211 | A1 | 11/2020 | Chee | |

FOREIGN PATENT DOCUMENTS

| | | | |
|---|---|---|---|
| EP | 1355598 | A2 | 6/2001 |
| EP | 1742579 | A1 | 4/2005 |
| EP | 2031362 | B1 | 8/2008 |
| EP | 2226010 | B1 | 2/2010 |
| EP | 2399521 | B1 | 6/2010 |
| EP | 3106143 | B1 | 6/2016 |
| EP | 3482734 | B1 | 6/2016 |
| EP | 3558205 | A1 | 12/2017 |
| EP | 3668470 | A1 | 8/2018 |
| JP | 2007534396 | A | 11/2007 |
| KR | 10-2310553 | B1 | 10/2021 |
| WO | WO01/95841 | A2 | 12/2001 |
| WO | WO2005/102173 | A1 | 11/2005 |
| WO | WO 2012/025829 | A2 | 3/2012 |
| WO | WO2018/119394 | A1 | 6/2018 |
| WO | WO2019/035762 | A1 | 2/2019 |
| WO | WO 2021/163147 | A1 | 8/2021 |

OTHER PUBLICATIONS

R. M. Nelson and H. Ji, "Electric and magnetic fields created by electrosurgical units," in IEEE Transactions on Electromagnetic Compatibility, vol. 41, No. 1, pp. 55-64, Feb. 1999, doi: 10.1109/15.748138.

Zhang, Y. T., and R. M. Rangayyan. "Adaptive cancellation of muscle contraction interference in vibroarthrographic signals." IEEE transactions on biomedical engineering 41.2 (1994): 181-191.

* cited by examiner

RADIOLUCENT SENSOR EMI SHIELDING

FIELD OF THE INVENTION

The present invention is directed to radiolucent pressure-sensing mattresses and methods of assembly thereof.

BACKGROUND OF THE INVENTION

The present invention is directed to radiolucent pressure-sensing mattresses and methods of assembly thereof.

SUMMARY OF THE INVENTION

In embodiments, a radiolucent pressure-sensing mattress for a surgical table includes a radiolucent sensor mat comprising radiolucent pressure sensors; a radiolucent ergonomic pad below the radiolucent sensor mat; a radiolucent fire protection layer enveloping the radiolucent pressure sensors and the radiolucent ergonomic pad; a radiolucent electromagnetic interference shielding layer enveloping the radiolucent fire protection layer, comprising woven carbon fiber; a shielding layer ground wire attached to the radiolucent electromagnetic interference shielding layer; a wire harness configured to connect the radiolucent sensor mat to a computer, the wire harness comprising a connection to the shielding layer ground wire, the wire harness comprising a master ground wire configured to connect to a grounding electrode of a hospital; and a radiolucent outer layer enveloping the radiolucent electromagnetic interference shielding layer.

In embodiments, the radiolucent pressure sensors are configured in a row and column array configured to be excited and measured via electronics integrated into the sensor mat. In embodiments, the row and column array includes a grid of sensors spaced at intervals of approximately one inch.

In embodiments, the radiolucent sensor mat further includes a first sheet having a plurality of first conductive paths, a layer of sensing material positioned in contact with the first conductive paths, a second sheet positioned in contact with the layer of sensing material, and a controller configured to detect changes in measurements of electrical characteristics measured by the layer of sensing material.

In embodiments, the radiolucent outer layer includes a first outer layer disposed along a top side and along four lateral sides of the radiolucent electromagnetic interference shielding layer, and a second outer layer disposed along a bottom side of the electromagnetic interference shielding layer.

In embodiments, the second outer layer includes weldable urethane laminated 210 denier nylon and the second outer layer is bonded to the first outer layer. In embodiments, the radiolucent ergonomic pad includes three layers of viscoelastic foam. In embodiments, the radiolucent fire protection layer further includes polyester rib fabric.

In embodiments, the radiolucent electromagnetic interference shielding layer is configured to shield the radiolucent sensor mat from electromagnetic interference emanating from an electrocautery device.

In embodiments, the woven carbon fiber further includes a dry fabric weight of approximately 5-7 oz/yd$^2$; a warp count of approximately 11 to 13 per inch; a fabric thickness of approximately 8-20 mil; a fill count of approximately 11 to 13 per inch; and approximately 2,500 to 3,500 carbon filaments.

Certain embodiments include a method of detecting pressure exerted by a patient's body on a hospital bed during a procedure wherein an electro-cautery device is being used in proximity to the hospital bed, comprising: providing a radiolucent pressure-sensing mattress, comprising: a radiolucent sensor mat comprising radiolucent pressure sensors; a radiolucent ergonomic pad below the radiolucent sensor mat; a radiolucent fire protection layer enveloping the radiolucent pressure sensors and the radiolucent ergonomic pad; a radiolucent electromagnetic interference shielding layer enveloping the radiolucent fire protection layer, comprising woven carbon fiber; a shielding layer ground wire attached to the radiolucent electromagnetic interference shielding layer; a wire harness configured to connect the radiolucent sensor mat to a computer, the wire harness comprising a connection to the shielding layer ground wire, the wire harness comprising a master ground wire configured to connect to a grounding electrode of a hospital; and a radiolucent outer layer enveloping the radiolucent electromagnetic interference shielding layer.

In embodiments, the radiolucent pressure sensors further includes a row and column array configured to be excited and measured by electronics integrated into the sensor mat.

In embodiments, the radiolucent pressure sensors are configured in an orientation comprising a grid of sensors spaced at intervals of approximately one inch.

In embodiments, the radiolucent outer layer includes a first outer layer disposed along a top side and along four lateral sides of the radiolucent electromagnetic interference shielding layer, and a second outer layer disposed along a bottom side of the electromagnetic interference shielding layer. In embodiments, the radiolucent ergonomic pad includes three layers of viscoelastic foam. In embodiments, the radiolucent fire protection layer further includes polyester rib fabric.

In embodiments, the woven carbon fiber further includes a dry fabric weight of approximately 5-7 oz/yd$^2$; a warp count of approximately 11 to 13 per inch; a fabric thickness of approximately 8-20 mil; a fill count of approximately 11 to 13 per inch; and approximately 2,500 to 3,500 carbon filaments.

In embodiments, a radiolucent pressure-sensing mattress for a surgical table includes a radiolucent sensor mat comprising radiolucent pressure sensors; a radiolucent ergonomic pad below the radiolucent sensor mat; a radiolucent fire protection layer enveloping the radiolucent pressure sensors and the radiolucent ergonomic pad; a radiolucent electromagnetic interference shielding layer enveloping the radiolucent fire protection layer; a shielding layer ground wire attached to the radiolucent electromagnetic interference shielding layer; a wire harness configured to connect the radiolucent sensor mat to a computer, the wire harness comprising a connection to the shielding layer ground wire, the wire harness comprising a master ground wire configured to connect to a grounding electrode of a hospital; and a radiolucent outer layer enveloping the radiolucent electromagnetic interference shielding layer.

In embodiments, the electromagnetic interference shielding layer includes a material selected from the group comprising woven carbon fiber, silver-laced fabric and conductive plastic.

DETAILED DESCRIPTION

Figure 1:
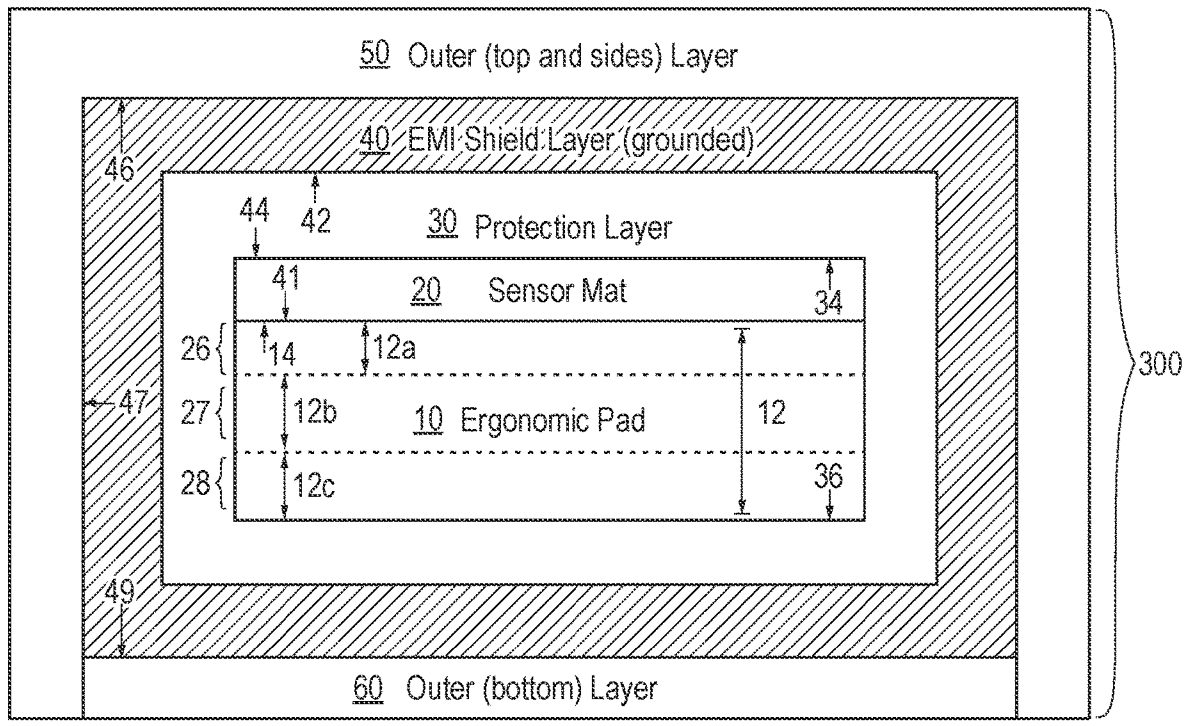
FIG. 1 is a cross-sectional view of an embodiment of a radiolucent pressure-sensing mattress.

In the following detailed description of embodiments, reference is made to the accompanying drawings, which form a part hereof and in which are shown, by way of illustration, specific embodiments in which the invention may be practiced. Specific details disclosed herein are in every case a non-limiting embodiment representing concrete ways in which the concepts of the invention may be practiced. This serves to teach one skilled in the art to employ the present invention in virtually any appropriately detailed system, structure or manner consistent with those concepts. It will be seen that various changes and alternatives to the specific described embodiments and the details of those embodiments may be made within the scope of the invention. Because many varying and different embodiments may be made within the scope of the inventive concepts herein described and in the specific embodiments herein detailed without departing from the scope of the present invention, it is to be understood that the details herein are to be interpreted as illustrative and not as limiting.

The various directions such as "upper," "lower," "bottom," "top," "back," "front," "perpendicular", "vertical", "horizontal," "length" and width" and so forth used in the detailed description of embodiments are made only for easier explanation in conjunction with the drawings to express the concepts of the invention. The elements in embodiments may be oriented differently while performing the same function and accomplishing the same result as obtained with the embodiments herein detailed, and such terminologies are not to be understood as limiting the concepts which the embodiments exemplify.

As used herein, the use of the word "a" or "an" when used in conjunction with the term "comprising" (or the synonymous "having" or "including") in the claims and/or the specification may mean "one," but it is also consistent with the meaning of "one or more," "at least one," and "one or more than one." In addition, as used herein, the phrase "connected to" means joined to or placed into communication with, either directly or through intermediate components.

Radiolucent Pressure-Sensing Mattress

Embodiments of the present invention include a radiolucent pressure-sensing mattress 300. The radiolucent pressure-sensing mattress 300 provides support for the patient's body during surgical procedures. The radiolucent pressure-sensing mattress 300 is placed upon a surgical table 80 before the patient is placed on the surgery table 80. The radiolucent pressure-sensing mattress 300 includes pressure sensors 22. These pressure sensors 22 measure the amount of force exerted by the patient's body at certain locations on the radiolucent pressure-sensing mattress 300. These measurements can assist medical professionals in preventing injuries, improve recovery, and provide other additional benefits.

As used herein, the term radiolucent means that an object is permeable to one or another form of radiation, and in particular, X-rays. Radiolucent objects may be permeable to other medical imaging radiation, including CT scans and PET scans, in addition to X-rays. Radiolucent objects do not block radiation but let it pass. Radiation is allowed to pass through radiolucent objects enough so as to not impede imaging. In certain embodiments, radiolucent objects do not allow all radiation to pass through. The opposite of radiolucent is radiopaque. Therefore in certain embodiments, radiolucent materials are not radiopaque. X-ray radiation is used in order to view the internal structure of a patient's body. Radiolucency is beneficial in order to allow for radiation that is used during a medical procedure, such as X-ray radiation, to pass through objects, and not obscure an X-ray image of a patient. If certain objects were not radiolucent, certain areas or angles of the patient's body may be unviewable or obscured in an X-ray image, because they are blocked or otherwise obscured by radiopaque or non-radiolucent materials.

The radiolucency of the radiolucent objects may be greater when the objects are more radiouniform. Radiouniformity is the consistency of the radiolucency of various parts of a radiolucent object. In certain embodiments, the mattress 300 and all of its components should not interfere with the clinician's diagnostic ability to read an image taken with the mattress 300 in the imaging field. If there is some interference in the image due to the mattress 300, it should be substantially consistent such that changes in image intensity can be attributed to the object being imaged and not variation in radiouniformity of the mattress 300 and all of its components. In embodiments, the radiolucent objects contain no metal. In embodiments, the radio-attenuation is minimal. In other embodiments, radio-attenuation is minimal compared to an embodiment that does not have shielding layer 40. Radio-attenuation is the measurement of the loss of intensity through a medium. Minimizing radio-attenuation results in preserving the greatest radiation through the radiolucent objects.

In accordance with the present invention, embodiments of a pressure-sensing mattress 300 including radiolucent electromagnetic interference shielding elements 40 allow for pressure sensors 22 incorporated into the mattress to function in a medical procedure without interference from electromagnetic interference, and also while being radiolucent.

In embodiments, the radiolucent pressure-sensing mattress 300 includes at least one or more of a radiolucent sensor mat 20, a radiolucent ergonomic pad 10, a radiolucent fire protection layer 30, a radiolucent electromagnetic interference shielding layer 40, a wire harness 100, and a radiolucent outer layer 50, 60.

Certain embodiments of the present disclosure include a method of detecting pressure exerted by a patient's body on a hospital bed during a medical procedure wherein an electro-cautery device is being used in proximity to the hospital bed, including the steps of: providing a radiolucent pressure-sensing mattress 300, embodiments of which are described herein. Certain embodiments include connecting the wire harness 100 to the radiolucent sensor mat 20 and to a computer 25 in the operating room, placing the radiolucent pressure-sensing mattress 300 on a surgical table 80, connecting the master ground wire 39 to the ground circuit of a hospital, and operating an electrocautery device.

Radiolucent Sensor Mat

As depicted generally in FIG. 1, in certain embodiments, the radiolucent pressure-sensing mattress 300 includes a radiolucent sensor mat 20. The radiolucent sensor mat 20 may include radiolucent pressure sensors 22 incorporated into the radiolucent sensor mat 20. The radiolucent sensor mat 20 may further include a flexible material. The radiolucent sensor mat 20 may further include a non-stretchable material. The radiolucent sensor mat 20 may provide a pressure distribution map. The radiolucent sensor mat 20 has the added benefit of not impeding the comfort provided to the patient by the ergonomic pad 10.

In certain embodiments, the radiolucent sensor mat 20 includes radiolucent pressure sensors 22. In embodiments, the radiolucent pressure sensors 22 are both functional as pressure sensors, and are also radiolucent so as to not interfere with medical imaging. The radiolucent pressure sensors 22 are configured to measure pressure exerted on the sensors by a patient's body. The radiolucent pressure sensors 22 are configured in any configuration suitable to detect the pressure exerted at relevant locations of the patient's body. Radiolucent pressure sensors 22 measure the detected pressures at the at least one relevant locations. In certain embodiments, the radiolucent pressure sensors 22 are connected to a computer 25. The computer 25 receives the measured pressure values from the radiolucent pressure sensors 22 and generates a map of the pressure values. This map can be used to guide any necessary adjustments to the patient's body. In additional embodiments, this map can be used to avoid potential injuries that may result from certain portions of the patient's body receiving pressure in excess of a threshold amount, and/or for an excess of a threshold time, which may cause tissue and/or nerve damage to the patient. In additional embodiments, the radiolucent pressure sensors 22 are configured to measure and map the distribution of the patient's weight, which can aid in making adjustments of the patient's body on the table, identify potential locations that are at risk of injury, and plan potential courses of treatment.

Figure 2:
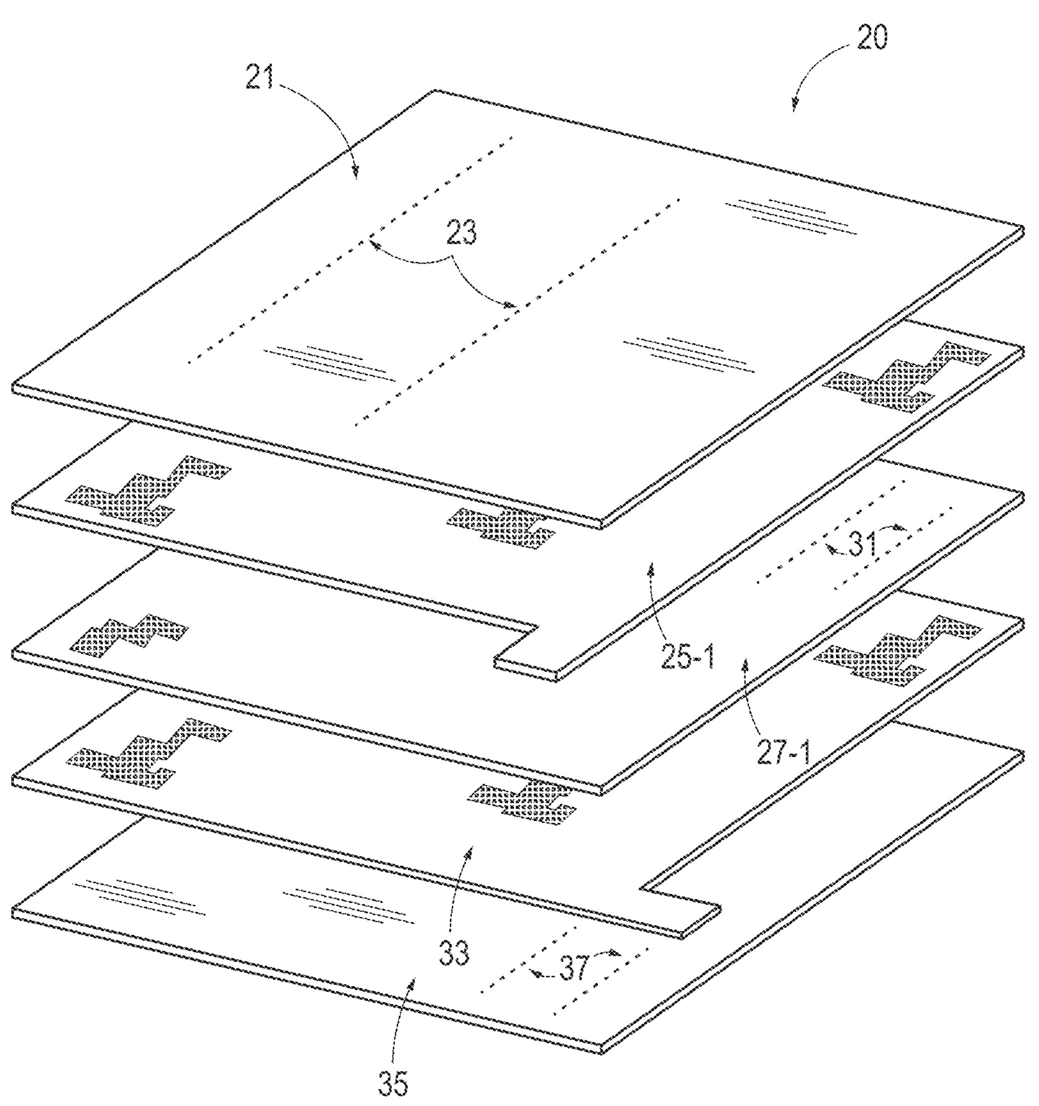
FIG. 2 is an exploded view of an embodiment of a radiolucent sensor mat.
Figure 3:
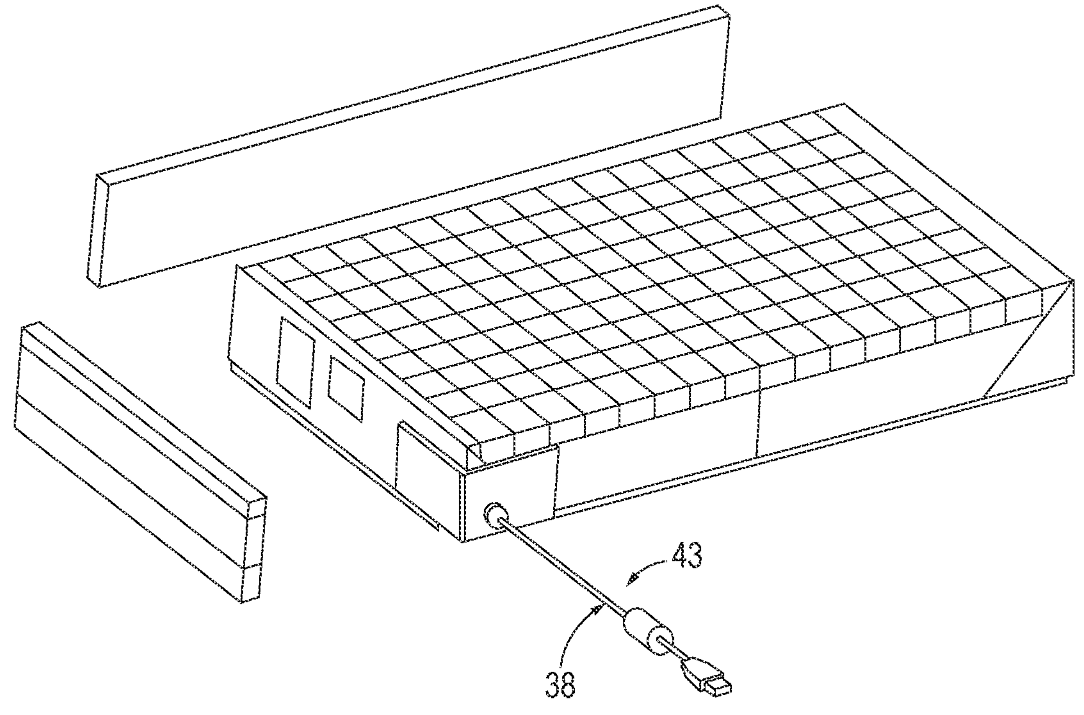
FIG. 3 is a perspective view of an embodiment of electronics integrated into a radiolucent sensor mat.

In an embodiment shown in FIG. 2, the radiolucent sensor mat 20 includes a mat 20 described in U.S. Pat. No. 8,997,588 ("Taylor"), which is incorporated by reference in its entirety herein. In one embodiment, a sensor mat 20 may include a first sheet 21 having a plurality of first conductive paths 23, a layer of sensing material 25-1 positioned in contact with said first conductive paths 23, a second sheet 27-1 positioned in contact with said layer of sensing material 25-1, and a controller 29 adapted to detect changes in measurements of electrical characteristics measured by the layer of sensing material 25-1. In certain embodiments, the sensor mat 20 may include a first sheet 21 having a plurality of first conductive paths 23, a first layer of sensing material 25-1 positioned in contact with said first conductive paths 23, a second sheet 27-1 having a plurality of second conductive paths 31, a second layer of sensing material 33, and a third sheet 35 having a plurality of third conductive paths 37.

Figure 4:
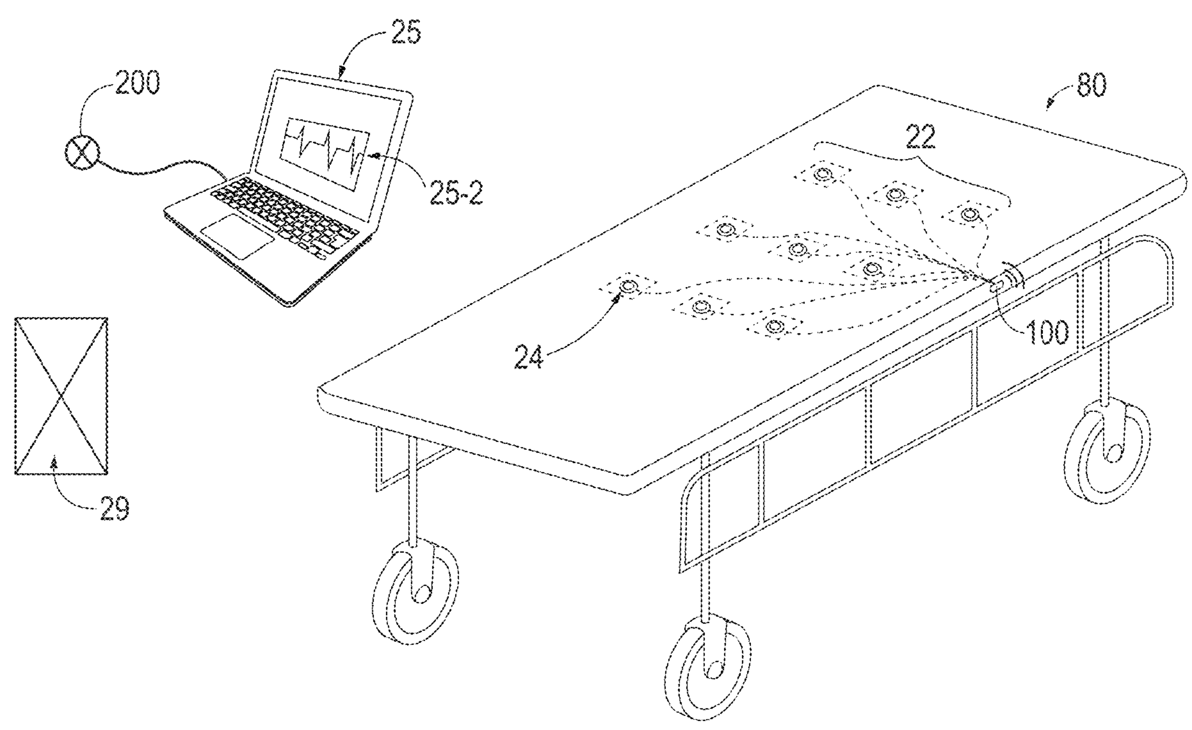
FIG. 4 is a perspective view of an embodiment of radiolucent sensors integrated into a surgical table and configured to convey measurements detected by the radiolucent sensors to a computer.
Figure 5:
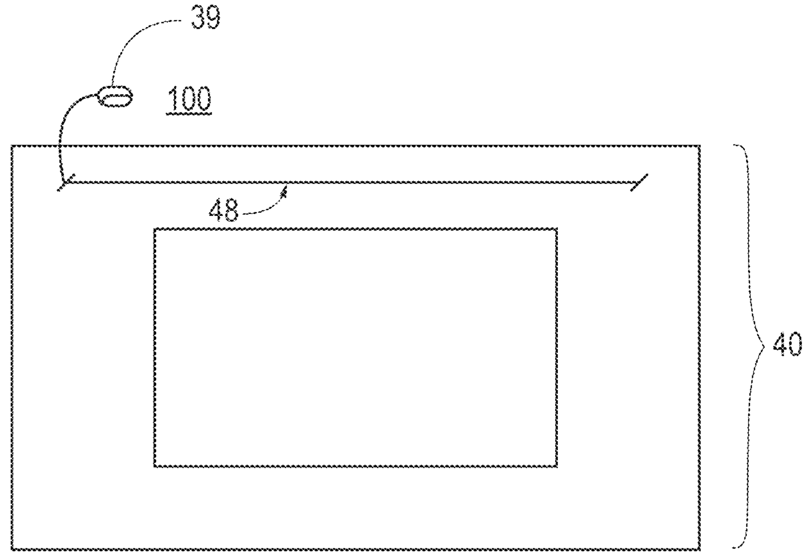
FIG. 5 is a cross-sectional view of a grounding wire integrated into a radiolucent electromagnetic interference shielding layer.

In embodiments as shown in FIG. 4, the radiolucent pressure sensors 22 include a row and column array configured to be excited and measured via electronics 24 integrated into the sensor mat 20. The row and column array may include sensors 22 configured in a grid pattern. The electronics 24 integrated into the sensor mat 20 may be configured to measure the signal detected by the sensors 22.

In certain embodiments, the electronics 24 integrated into the sensor mat 20 may also include a cable 43 that exits the ergonomic pad 10. The cable 43 communicates information from sensors 22 to a computer 25, or some other controller 29 or device. The cable 43 can include a USB cable, an Ethernet cable, or other cable. The cable 43 may further include a shielded cable including a grounded shield 38. A shielded cable is an electrical cable that has a common conductive layer around its conductors for electromagnetic interference shielding. In certain embodiments, this shield includes an outermost layer of the cable. Common types of cable shielding can most broadly be categorized as foil type including metallised film, contraspiralling wire strands (braided or unbraided), such as braided strands of copper (or other metal, such as aluminum), a non-braided spiral winding of copper tape, a layer of conducting polymer, and combinations of any of the foregoing. In some embodiments, the shield acts as a Faraday cage, or a surface that reflects electromagnetic radiation. This reduces both the interference from outside noise onto the signals in the cable, and the signals in the cable from radiating out and potentially disturbing other devices. To be effective against electric fields, the shield must be grounded. The shield should be electrically continuous to maximize effectiveness.

In embodiments, the radiolucent sensor mat 20 further includes an active portion and an inactive portion wherein the active portion comprises electronic components such as connectors, wiring, transmitters, and any other component that is not a sensor. The electronic components may be folded out of the way of the patient's body. The inactive portion of the radiolucent sensor mat comprises the radiolucent pressure sensors 22. The radiolucent pressure sensors 22 may be placed on the top side 14 the ergonomic pad 10 and the electronic components can be disposed on the lateral sides of the ergonomic pad 10, where they will not contact a patient's body. In embodiments, the radiolucent pressure sensors 22 may be placed only on the top side 14 the ergonomic pad 10, and the electronic components are on a portion of the sensor mat 20 that is folded over and located on the lateral sides of the ergonomic pad 10, where they will not contact a patient's body. In embodiments, the radiolucent sensor mat 20 is incorporated into the ergonomic pad 10.

In embodiments the radiolucent pressure sensors 22 include the pressure sensors being configured to be a grid of readings spaced at intervals selected to balance cost and image resolution of the resultant pressure map. In embodiments, the radiolucent pressure sensors 22 include the pressure sensors being configured to be a grid of readings spaced at intervals that are approximately one inch on center. In other words, one inch from center intersection to center intersection, where the sensors are lined up in a row and column arrangement.

Radiolucent Ergonomic Pad

In certain embodiments, the radiolucent pressure-sensing mattress 300 includes a radiolucent ergonomic pad 10. In some embodiments, the radiolucent ergonomic pad 10 is located between the surgical table 80 and the patient's body. In other embodiments, the radiolucent ergonomic pad 10 is located between the surgical table 80 and the sensor mat 20. The radiolucent ergonomic pad 10 may provide additional cushioning and support to the patient's body. The radiolucent ergonomic pad 10 can include foam, memory foam including low-resistance polyurethane foam, or other materials that provide cushioning and/or support.

The radiolucent ergonomic pad 10 may have a thickness 12 that is sufficient to provide support for the patient's body. The ergonomic pad 10 may provide comfort and prevent injury to the patient's body during surgery. In some embodiments, the ergonomic pad 10 is disposed below the radiolucent sensor mat 20. In these embodiments, at least a portion of a top side 14 of the ergonomic pad 10 is in contact with at least a portion of a bottom side 41 of the radiolucent sensor mat 20. In embodiments, the radiolucent ergonomic pad 10 includes at least one layer of material. In embodiments, the radiolucent ergonomic pad 10 includes at least one layer of viscoelastic foam 26.

In some embodiments, the radiolucent ergonomic pad 10 includes three layers of viscoelastic foam 26, 27, 28. The first layer of viscoelastic foam 26 includes a first thickness 12*a*, the second layer of viscoelastic foam 27 includes a second thickness 12*b*, and the third layer of viscoelastic foam 28 includes a third thickness 12*c*. The three layers of viscoelastic foam 26, 27, 28 can include adhesive to connect the first layer 26 to the second layer 27 and the second layer 27 to the third layer 28. The first layer 26 is the most compliant while the bottom layer 28 is most stiff least compliant, to improve support for patients of various weights.

Radiolucent Fire Protection Layer

In certain embodiments, the radiolucent pressure-sensing mattress 300 includes a radiolucent fire protection layer 30. In some embodiments, not all mattress materials are flame retardant, therefore, fire protection layers 30 aids in slowing the spread of a fire that reaches the mattress 300. Fire protection layers 30 can include a layer of material treated with a chemical, or other natural or synthetic materials that are used to ensure that the mattress meets flammability standards. Such chemicals can include Polybrominated Diphenyl Ethers (PBDEs). In certain embodiments, the radiolucent fire protection layer 30 envelops the radiolucent sensor mat 20 and the ergonomic pad 10. In some embodiments, the radiolucent fire protection layer 30 includes polyester rib fabric. In other embodiments, the radiolucent fire protection layer 30 envelops any of the other layers as described herein, including the sensor mat 20, the ergonomic pad 10, and the electromagnetic interference shielding layer 40.

As used herein, the term "envelops" means that a layer surrounds another layer or layers as described herein. In certain embodiments, a layer that envelops provides an encasement. An encasement is a unitary layer that surrounds all sides of the other layers that it envelops. In other embodiments, a layer that envelops includes at least one sheet. In certain embodiments, envelops means that a layer surrounds another layer or layers on all sides, with or without being unitary. In other embodiments, a layer that envelops is disposed both above and below the other layer or layers. Such layer may include an outer side 42 and an inner side 44. The inner side 44 contacts a top side 34 of the other layer or layers and a bottom side 36 of the other layer or layers. In embodiments, the layer or layers that are enveloped by another layer are inserted into the enveloping layer through at least one open side. After the layer or layers is placed within the enveloping layer, the at least one open side of the enveloping layer may be sealed. The at least one open side can be sealed by forming a seam, including by folding, sewing, a zipper, hook and loop, ultrasonic welding, heat-sealing, an adhesive, stitching, snaps, buttons, or otherwise. In other embodiments, the at least one open side of the enveloping layer is not sealed after placement of the other layers within the enveloping layer. In certain embodiments, the at least one open side of the enveloping layer is folded.

In some embodiments, the radiolucent fire protection layer 30 envelops the radiolucent ergonomic pad 10 and radiolucent sensor mat 20. In other embodiments, the radiolucent fire protection layer 30 is disposed both above and below the radiolucent ergonomic pad 10 and radiolucent sensor mat 20. In certain embodiments, the radiolucent fire protection layer 30 has an outer side 42 and an inner side 44. The inner side 44 contacts a top side 34 of the radiolucent sensor mat 20 and a bottom side 36 of the ergonomic pad 10. In other embodiments, at least one open side of the radiolucent fire protection layer 30 is not sealed after placement of the radiolucent ergonomic pad 10 and radiolucent sensor mat 20 within the radiolucent fire protection layer 30.

Radiolucent Electromagnetic Interference (EMI) Shielding Layer

In some embodiments, the radiolucent electromagnetic interference shielding layer 40 envelops the radiolucent fire protection layer 30. In embodiments, the radiolucent electromagnetic interference shielding layer 40 is configured to shield electrical components of the mattress from electromagnetic interference (EMI). EMI can be caused by electromagnetic fields, which are generated by electrical devices, such as those used in surgery. Shielding reduces and/or blocks such interference. EMI shielding blocks or reduces the electromagnetic field (EMF) in a space with barriers made of conductive or magnetic materials. In some embodiments, EMI shielding isolates electrical devices from their surroundings. EMI shielding may minimize electromagnetic interference. A conductive enclosure used to block electrostatic fields may be known as a Faraday cage.

In embodiments, the radiolucent electromagnetic interference shielding layer 40 includes carbon fiber. Carbon fiber is a fiber composed primarily of carbon atoms. Carbon fiber is produced by bonding together carbon atoms into crystals that are arranged predominately along one axis. These crystals form individual fibers. These individual fibers can be twisted together into tows.

In embodiments, the resultant tows of carbon fiber can be arranged into a fabric composite wherein the individual fibers are either unidirectional or woven. Woven composites of the carbon fiber tows can be plain weaves, harness satin weaves, or twill weaves. In certain embodiments, the radiolucent electromagnetic interference shielding layer 40 includes woven carbon fiber. In embodiments, the woven carbon fiber of the radiolucent electromagnetic interference shielding layer 40 includes a 2×2 twill weave carbon fiber fabric.

In one embodiment, the carbon fiber weave style is a 2×2 twill, and includes a dry fabric weight of the carbon fiber is 5.80 oz/yd$^2$, the warp count of the carbon fiber is 12/inch, the fill count of the carbon fiber is 12/inch, the fabric thickness of the carbon fiber is 9.1 mil, and the carbon fiber comprises 3,000 carbon filaments.

In another embodiment, the carbon fiber weave style is a 2×2 twill, and includes a dry fabric weight of the carbon fiber is 6.5 oz/yd$^2$, the warp count of the carbon fiber is 12/inch, the fill count of the carbon fiber is 12/inch, the fabric thickness of the carbon fiber is 18.1 mil, and the carbon fiber comprises 3,000 carbon filaments.

In embodiments, the dry fabric weight of the carbon fiber is from 5.80-6.5 oz/yd$^2$. In other embodiments, the dry fabric weight of the carbon fiber is from 5-7 oz/yd$^2$, and in still other embodiments, the dry fabric weight of the carbon fiber is from 4-8 oz/yd$^2$, and in other embodiments, 2-10 oz/yd$^2$.

In embodiments, the warp count of the carbon fiber is approximately 12/inch. In other embodiments, the warp count of the carbon fiber is approximately 11-13/inch, and in other embodiments, 10-14 per inch.

In embodiments, the fill count of the carbon fiber is approximately 12/inch. In other embodiments, the fill count of the carbon fiber is approximately 11-13/inch, and in other embodiments, 10-14 per inch.

In embodiments, the fabric thickness of the carbon fiber is from 9.1-18.1 mil. In other embodiments, and the fabric thickness of the carbon fiber is from 8-20 mil, and in other embodiments, the fabric thickness of the carbon fiber is from 6 to 22 mil, 5 to 25 mil, or 2-30 mil.

In embodiments, the carbon fiber comprises approximately 3,000 carbon filaments. In other embodiments, the carbon fiber comprises approximately 2,800-3,200 carbon filaments. In still further embodiments, the carbon fiber comprises approximately 2,500-3,500, or 2,000-4,000 carbon filaments.

In other embodiments, the EMI shielding layer includes sheet metal (include copper, brass, nickel, silver, steel, and tin), metal screen, woven metal fibers, metal foam, a coating metallic ink or similar material.

In embodiments, the radiolucent electromagnetic interference shielding layer 40 includes a grounding wire 48 attached to the radiolucent electromagnetic interference shielding layer 40. In some embodiments, the grounding wire 48 can be crimped to the radiolucent electromagnetic interference shielding layer 40. In other embodiments, the grounding wire 48 can be soldered or sewn to the radiolucent electromagnetic interference shielding layer 40. In embodiments, the grounding wire 48 includes an electrically conductive material and an insulating material. In embodiments, the electrically conductive material includes copper. In embodiments, the grounding wire can be attached to the radiolucent electromagnetic interference shielding layer 40 at one or more bonding locations. In embodiments, the wire harness 100 includes a connection to the grounding wire 48, the wire harness 100 comprising a master ground wire 39 configured to connect to a grounding electrode of a hospital. In certain embodiments, the wire harness 100 is routed through an opening in the fire protection layer 30, radiolucent electromagnetic interference shielding layer 40, and outer layer 50, 60.

In embodiments, the wire harness 100 includes a connection at a first end to the radiolucent sensor mat 20, and at a second end to a sensor control board 25-2. In embodiments, the sensor control board 25-2 is configured to receive data from the radiolucent pressure sensors 22. In embodiments, the sensor control board 25-2 includes a further connection to a grounded location 200. In embodiments, the wire harness 100 forms the connection between the radiolucent electromagnetic interference shielding layer 40 and the radiolucent sensor mat 20 and the connection between the radiolucent electromagnetic interference shielding layer 40 and the sensor control board 25-2.

In embodiments, the radiolucent electromagnetic interference shielding layer 40 is configured to shield the radiolucent sensor mat 20 from electromagnetic interference emanating from an electrocautery device.

Wire Harness

In embodiments, the wire harness 100 is configured to connect the radiolucent sensor mat 20 to a computer 25, controller 29, or other device in the operating room. In embodiments, the wire harness 100 includes a connection to the electromagnetic interference shielding layer ground wire 39 and the sensor mat 20. In embodiments, the wire harness includes a master ground wire 39 configured to connect to the grounding electrode of a hospital, wherein the EMI collected by the EMI shielding layer can be grounded. In embodiments, the ground wire 39 is a ductile conductive material. In embodiments, the ground wire 39 is copper. In embodiments, the computer 25, controller 29, or other device connects to the grounding electrode of a hospital. In certain embodiments where the wire harness is connected to the grounding electrode of a hospital via the master ground wire 39, the pressure sensors 22 communicate wirelessly to a computer 25, or some other controller 29 or device, and there is no wired connection to a computer.

Radiolucent Outer Layer

In certain embodiments, the radiolucent pressure-sensing mattress 300 includes a radiolucent outer layer 50, 60. The radiolucent outer layer envelops the radiolucent electromagnetic interference shielding layer. The radiolucent outer layer provides biocompatibility with a patient, support, protection from fluid ingress, and the ability to be removed and cleaned without needing to clean the remaining components of mattress 300.

In embodiments, the radiolucent outer layer 50, 60 includes a first outer layer 50 disposed along a top side 46 and along four lateral sides 47 of the radiolucent electromagnetic interference shielding layer 40, and a second outer layer 60 disposed along a bottom side 49 of the electromagnetic interference shielding layer 40.

In embodiments, the first outer layer 50 includes a polyurethane coated polyester knit.

In embodiments, the second outer layer 60 includes weldable urethane laminated 210 denier nylon. In embodiments, the second outer layer 60 includes a connection to the first outer layer 50. In embodiments, the connection between the first outer layer 50 and the second outer layer 60 includes a bonded connection. The bonded connection can be formed by forming a seam, including by folding, sewing, a zipper, hook and loop, ultrasonic welding, heat-sealing, an adhesive, stitching, snaps, buttons, or otherwise.

I claim:

1. A radiolucent pressure-sensing mattress for a surgical table comprising:

- a radiolucent sensor mat comprising radiolucent pressure sensors;
- a radiolucent ergonomic pad below the radiolucent sensor mat;
- a radiolucent fire protection layer enveloping the radiolucent pressure sensors and the radiolucent ergonomic pad;
- a radiolucent electromagnetic interference shielding layer comprising woven carbon fiber enveloping the radiolucent fire protection layer;
- a shielding layer ground wire attached to the radiolucent electromagnetic interference shielding layer;
- a wire harness configured to connect the radiolucent sensor mat to a computer, the wire harness comprising a connection to the shielding layer ground wire, the wire harness comprising a master ground wire configured to connect to a grounding electrode of a hospital; and
- a radiolucent outer layer enveloping the radiolucent electromagnetic interference shielding layer.

2. The radiolucent pressure-sensing mattress of claim 1, the radiolucent pressure sensors configured in a row and column array configured to be excited and measured via electronics integrated into the radiolucent sensor mat.

3. The radiolucent pressure-sensing mattress of claim 2, the row and column array comprising a grid of sensors spaced at intervals of approximately one inch.

4. The radiolucent pressure-sensing mattress of claim 2, the radiolucent sensor mat further comprising:

- a first sheet having a plurality of first conductive paths, a layer of sensing material positioned in contact with the first conductive paths, a second sheet positioned in contact with the layer of sensing material, and a controller configured to detect changes in measurements of electrical characteristics measured by the layer of sensing material.

5. The radiolucent pressure-sensing mattress of claim 1 wherein the radiolucent outer layer comprises a first outer layer disposed along a top side and along four lateral sides of the radiolucent electromagnetic interference shielding layer, and a second outer layer disposed along a bottom side of the electromagnetic interference shielding layer.

6. The radiolucent pressure-sensing mattress of claim 5, the first outer layer comprising a polyurethane coated polyester knit.

7. The radiolucent pressure-sensing mattress of claim 5, the second outer layer comprising weldable urethane laminated 210 denier nylon, and wherein the second outer layer is bonded to the first outer layer.

8. The radiolucent pressure-sensing mattress of claim 1, the radiolucent ergonomic pad comprising three layers of viscoelastic foam.

9. The radiolucent pressure-sensing mattress of claim 1, the radiolucent fire protection layer further comprising polyester rib fabric.

10. The radiolucent pressure-sensing mattress of claim 1, the radiolucent electromagnetic interference shielding layer configured to shield the radiolucent sensor mat from electromagnetic interference emanating from an electrocautery device.

11. The radiolucent pressure-sensing mattress of claim 1, the woven carbon fiber further comprising:

a 2×2 twill weave;
a dry fabric weight of approximately 5-7 oz/yd$^2$;
a warp count of approximately 11 to 13 per inch;
a fabric thickness of approximately 8-20 mil;
a fill count of approximately 11 to 13 per inch; and
approximately 2,500 to 3,500 carbon filaments.

12. A method of detecting pressure exerted by a patient's body on a hospital bed during a procedure wherein an electro-cautery device is being used in proximity to the hospital bed, comprising:

providing a radiolucent pressure-sensing mattress, comprising:
a radiolucent sensor mat comprising radiolucent pressure sensors;
a radiolucent ergonomic pad below the radiolucent sensor mat;
a radiolucent fire protection layer enveloping the radiolucent pressure sensors and the radiolucent ergonomic pad;
a radiolucent electromagnetic interference shielding layer enveloping the radiolucent fire protection layer, comprising woven carbon fiber;
a shielding layer ground wire attached to the radiolucent electromagnetic interference shielding layer;
a wire harness configured to connect the radiolucent sensor mat to a computer, the wire harness comprising a connection to the shielding layer ground wire, the wire harness comprising a master ground wire configured to connect to a grounding electrode of a hospital; and
a radiolucent outer layer enveloping the radiolucent electromagnetic interference shielding layer;
placing the radiolucent pressure-sensing mattress on a surgical table;
connecting the wire harness to the computer;
connecting the master ground wire to the grounding electrode of a hospital; and
operating the electro-cautery device.

13. The method of claim 12, the radiolucent pressure sensors further comprising a row and column array configured to be excited and measured by electronics integrated into the radiolucent sensor mat.

14. The method of claim 13, the radiolucent pressure sensors configured in an orientation comprising a grid of sensors spaced at intervals of approximately one inch.

15. The method of claim 12 wherein the radiolucent outer layer comprises a first outer layer disposed along a top side and along four lateral sides of the radiolucent electromagnetic interference shielding layer, and a second outer layer disposed along a bottom side of the radiolucent electromagnetic interference shielding layer.

16. The method of claim 12 the radiolucent ergonomic pad comprising three layers of viscoelastic foam.

17. The method of claim 12 the radiolucent fire protection layer further comprising polyester rib fabric.

18. The method of claim 12, the woven carbon fiber further comprising:

a 2×2 twill weave;
a dry fabric weight of approximately 5-7 oz/yd$^2$;
a warp count of approximately 11 to 13 per inch;
a fabric thickness of approximately 8-20 mil;
a fill count of approximately 11 to 13 per inch; and
approximately 2,500 to 3,500 carbon filaments.

19. A radiolucent pressure-sensing mattress for a surgical table comprising:

a radiolucent sensor mat comprising radiolucent pressure sensors;
a radiolucent ergonomic pad below the radiolucent sensor mat;
a radiolucent fire protection layer enveloping the radiolucent pressure sensors and the radiolucent ergonomic pad;
a radiolucent electromagnetic interference shielding layer enveloping the radiolucent fire protection layer;
a shielding layer ground wire attached to the radiolucent electromagnetic interference shielding layer;
a wire harness configured to connect the radiolucent sensor mat to a computer, the wire harness comprising a connection to the shielding layer ground wire, the wire harness comprising a master ground wire configured to connect to a grounding electrode of a hospital; and
a radiolucent outer layer enveloping the radiolucent electromagnetic interference shielding layer.

20. The pressure-sensing mattress of claim 19, the radiolucent electromagnetic interference shielding layer comprising a material selected from the group comprising woven carbon fiber, silver-laced fabric and conductive plastic.

* * * * *